(12) United States Patent
Kataoka et al.

(10) Patent No.: US 7,129,293 B2
(45) Date of Patent: Oct. 31, 2006

(54) CROSSLINKED POLYMERS, FINE POLYMER PARTICLE, AND PROCESS FOR PRODUCING THESE

(75) Inventors: Kazunori Kataoka, Tokyo (JP); Yukio Nagasaki, Moriya (JP); Hidenori Otsuka, Tsukuba (JP); Atsuhiko Ogura, Tsuchiura (JP); Takehiko Ishii, Washimiya-machi (JP); Hisato Hayashi, Matsudo (JP); Teppei Uno, Hitachi (JP)

(73) Assignees: Japan Science and Technology Agency, Saitama (JP); NOF Corporation, Tokyo (JP)

( * ) Notice: Subject to any disclaimer, the term of this patent is extended or adjusted under 35 U.S.C. 154(b) by 0 days.

(21) Appl. No.: 10/512,424

(22) PCT Filed: Apr. 23, 2003

(86) PCT No.: PCT/JP03/05144

§ 371 (c)(1),
(2), (4) Date: Oct. 25, 2004

(87) PCT Pub. No.: WO03/091302

PCT Pub. Date: Nov. 6, 2003

(65) Prior Publication Data

US 2005/0171289 A1    Aug. 4, 2005

(30) Foreign Application Priority Data

Apr. 24, 2002  (JP) .............................. 2002-121850

(51) Int. Cl.
C08L 47/00 (2006.01)
C08L 132/00 (2006.01)
A61K 9/14 (2006.01)

(52) U.S. Cl. ..................... 525/69; 525/84; 525/118; 525/162; 525/326.1; 523/407; 424/486

(58) Field of Classification Search ................ 525/162, 525/118, 69, 84, 326.1; 424/486; 523/407
See application file for complete search history.

(56) References Cited

U.S. PATENT DOCUMENTS

| | | | |
|---|---|---|---|
| 6,306,610 B1 | 10/2001 | Bawendi et al. | |
| 6,410,004 B1 | 6/2002 | Kim et al. | |
| 6,696,089 B1 * | 2/2004 | Kabanov et al. | ............ 424/484 |
| 2004/0038506 A1 | 2/2004 | Kataoka et al. | |

FOREIGN PATENT DOCUMENTS

| | | |
|---|---|---|
| EP | 1035144 | 9/2000 |
| JP | 62-180745 | 8/1987 |
| JP | 08-133990 | 5/1996 |
| JP | 8-188541 | 7/1996 |
| JP | 9-78056 | 3/1997 |
| JP | 09-302048 | 11/1997 |
| JP | 10-317022 | 12/1998 |
| JP | 2001-152213 | 6/2001 |
| JP | 2001-192712 | 7/2001 |
| JP | 2001-200050 | 7/2001 |
| JP | 2002-80903 | 3/2002 |
| JP | 2002-211062 | 7/2002 |
| WO | 98/46655 | 10/1998 |
| WO | 00/76699 | 12/2000 |

OTHER PUBLICATIONS

English translation of originally filed PCT application (PCT/JP98/01599).
Kazunori Kataoka et al., "Polyion Complex Micelles with Reactive Aldehyde Groups on Their Surface from Plasmid DNA and End-Functionalized Charged Block Copolymers", Macromolecules, 32, pp. 6892-6894, 1999.
Hidenori Otsuka et al., Quantitative and Reversible Lectin-Induced Association of Gold Nanoparticles Modified with α-Lactosyl-ω-mercapto-poly(ethylene glycol), J. Am. Chem. Soc., 123, pp. 8226-8230, 2001.
Warren C.W. Chan et al., "Quantum Dot Bioconjugates for Ultrasensitive Nonisotopic Detection", Science, vol. 281, pp. 2016-2018, 1998.
Nataliya N. Mamedova et al. "Albumin-CdTe Nanoparticle Bioconjugates: Preparation, Structure, and Interunit Energy Transfer with Antenna Effect", Nano Letters, vol. 1, No. 6, pp. 282-286, 2001.

* cited by examiner

*Primary Examiner*—James J. Seidleck
*Assistant Examiner*—Olga Asinovsky
(74) *Attorney, Agent, or Firm*—Wenderoth, Lind & Ponack, L.L.P.

(57) ABSTRACT

A crosslinked polymer or polymer fine particles which can be obtained through copolymerization of at least a macromonomer having a polyethylene glycol segment, a comonomer having tertiary amine groups in its side chains and a crosslinking agent are provided. Said crosslinked polymer can be provided in the form of polymer nano- or micro-spheres; and also as conjugate nano- or micro-spheres with their core parts fixing or encapsulating metal or semiconductor ultrafine particles.

16 Claims, 4 Drawing Sheets
(1 of 4 Drawing Sheet(s) Filed in Color)

RUN10(Cd:N=1:12)  RUN11(Cd:N=1:1)  RUN12(Cd:N=1:2)

RUN13(Cd:N=1:5)  RUN14(Cd:N=1:8)  RUN15(Cd:N=1:12)

Photo. Width 0.28mm for all

CROSSLINKED POLYMERS, FINE POLYMER PARTICLE, AND PROCESS FOR PRODUCING THESE

TECHNICAL FIELD

This invention relates to crosslinked polymer fine particles which are useful as carriers for organic drug represented by oligo- or poly-nucleotide, and for ultrafine particles of inorganic substances represented by semiconductor, free electron metal or metal oxide; and relates also to their production processes and their use.

BACKGROUND ART

Copolymers provided by a part of the present inventors, for example, poly(ethylene glycol)-block-poly(dialkylaminoethyl methacrylate) form polymer micelle via an anionically charged polymer, and hence they are useful as carriers for anionically charged drug (cf. e.g., patent reference 1 and non-patent reference 1). They also can contribute to stabilize dispersions of colloidal gold or semiconductor fine particles, and can provide gold- or semiconductor-fixing (or encapsulating) polymer particles useful as markers or quantum dots in biological assay systems (cf. e.g., patent reference 2).

It is also known that poly(ethylene glycol) derivatives, in which poly(dialkylaminoethyl methacrylate) segment in above block copolymers is replaced with terminal mercapto groups, can be conveniently used for stabilizing dispersions of ultrafine particles of gold and semiconductors (see, for example, said patent references 2, 3 and 4 and non-patent reference 1). Furthermore, fine particles of a polymer having poly (oxyalkylene) segment, which are formed of a (meth) acrylic ester and styrene and are capable of encapsulating ultrafine inorganic particles serviceable as a marker in the polymer latex particles, are known to be stable in aqueous media and capable of suppressing non-specific adsorption of protein onto said latex particle surfaces (cf. patent reference 5). A part of the present inventors have also provided heterotelecheric polymers represented by, for example, a formula,

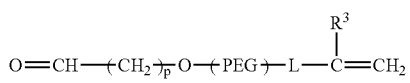

and copolymers of above polymers used as macromonomers, with styrene, (meth)acrylic acid or esters or amides thereof (cf. patent reference 6). These copolymers are a kind of graft polymers having PEG chains as branch polymers and, in addition to their functions achievable as graft polymers per se, can form conjugates with various biomolecules via aldehyde (O=CH—) groups at one of their terminals. They, therefore, are interesting as a biocompatible material.

LIST OF PRIOR ART REFERENCES

Patent reference 1: WO98/46655 Pamphlet (page 19, Example 8);
Patent reference 2: JP2002-80903A;
Patent reference 3: JP2001-20050A;
Patent reference 4: U.S. Pat. No. 6,306,610;
Patent reference 5: JP-Hei 8 (1996)-133990A;
Patent reference 6: JP-Hei 9 (1997)-302048A;

Non-patent reference 1: Kataoka et al., *Macromolecules* 1999, 32, 6892–6894;
Non-patent reference 2: Otsuka et al., *J. Am. Chem., Soc.,* 2001, 123, 8226–8230.

DISCLOSURE OF THE INVENTION

Said poly(ethylene glycol)-block-poly(dialkyl ethyl methacrylate) itself forms core-shell type structure, or favorable core-shell type conjugates or complexes with drug such as polynucleotide or fine particles of gold or semiconductor serving as the core, where their shells or surfacial parts are formed of the poly(ethylene glycol) chains. A certain kind of latex particles as disclosed in the patent references 5 and 6 can also contain, as encapsulated therein or fixed thereon, drug or fine particles of gold or semiconductor as their cores.

Whereas, if a carrier which can fix or encapsulate a drug or the like more stably but under predetermined environment can selectively release the fixed drug or the like is provided, it will contribute to provide a favorable drug delivery system, or quantum dot or marker having still additional functions. An object of the present invention is to provide such a carrier.

We have engaged in concentrative studies with the view to accomplish that object, to discover: where the core parts of polymer fine particles are amino-rich and have a network structure formed by cross-linkage, and the shell parts are formed of a monomer to supply said amino groups and a macromer having an independent poly(ethylene glycol) segment, such polymer fine particles could not only stably fix or encapsulate aforesaid drug in their core parts, but also could swell or, conversely, shrink according to environmental changes, for example, pH change in an aqueous medium, while retaining their core-shell structure, whereby facilitating selective release of said drug or the like. This invention is completed based on said discovery.

Accordingly, therefore, the invention provides polymer fine particles derived from a crosslinked polymer having main chains formed of ethylenically unsaturated polymerizable groups and crosslinkages between said main chains, which are characterized in that said main chain comprises (i) side chains each of N, N-di-C$_{1-6}$ alkyl-substituted amino group covalently bonded to said main chain via a linker formed of 1–10 atoms, and (ii) side chains each of a hydrophilic group having a poly (ethylene glycol) segment which is covalently bonded to said main chain, independently of each other;

the polymer fine particles thus forming core-shell type fine particles when solubilized or dispersed in an aqueous medium, said side chains (i) and the main chains chiefly forming the core parts and the side chains (ii) chiefly forming the shell parts.

The invention relates also to a crosslinked polymer from which such polymer fine particles can be conveniently formed. As another embodiment of the present invention, a crosslinked polymer which is obtained through copolymerization of (a) a poly(ethylene glycol) macromonomer represented by a formula I:

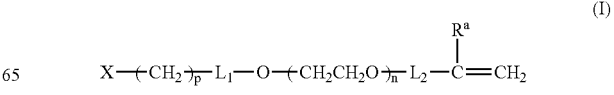

[in which X stands for hydrogen, —COOZ group (wherein Z standing for hydrogen or an organic group), —CHR¹R² (wherein R¹ and R² independently standing for $C_{1-6}$ alkyloxy, phenyloxy or phenyl-$C_{1-3}$ alkyloxy, or R¹ and R² together forming —OCHR'—CH₂O—, R' standing for hydrogen or $C_{1-6}$ alkyl) or —CH=O, $R^a$ stands for hydrogen or $C_{1-6}$ alkyl, $L_1$ stands for methylene or carbonyl, $L_2$ stands for carbonyl, $C_{1-3}$ alkylene or $C_{1-3}$ alkylphenylene, or X—(CH₂)$_p$-$L_1$-integrally stands for hydrogen or $C_{1-6}$ alkyl, n is an integer of 2–10,000, and p is an integer of 1–5]; with (b) a comonomer represented by a formula II:

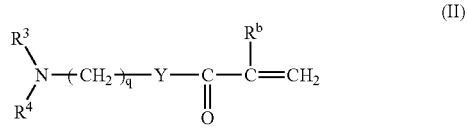

(in which $R^3$ and $R^4$ each independently stands for $C_{1-6}$ alkyl, $R^b$ stands for hydrogen or $C_{1-6}$ alkyl, Y stands for —O— or —NH—, and q is an integer of 2–6);

(c) a crosslinking agent having 2, 3, or more polymerizable unsaturated groups, and (d) optionally a diluent monomer having polymerizable unsaturated group other than (a) and (b). According to a specific embodiment of such a crosslinked polymer, a polymer in which said poly(ethylene glycol) macromonomer (a) and the comonomer (b) are present at a molar ratio ranging 1/400–, preferably 1/200–, in particular, 1/100–2/1, and the crosslinking agent is present at a ratio of 0.1–25 mol % to the total amount of said macromonomer (a) and comonomer (b) is provided.

According to the invention, furthermore, also provided are the polymer fine particles in whose core parts gold or semiconductor ultrafine particles of s size ranging 1 nm–40 nm are further fixed; or the polymer fine particles in whose core parts oligo- or poly-(nucleotide) or anionically charged drug is further fixed.

The invention furthermore provides a method for producing a crosslinked polymer, which comprises the steps of mixing in an inert atmosphere at room temperature (a) an aqueous solution containing a poly(ethylene glycol) macromonomer represented by the formula I:

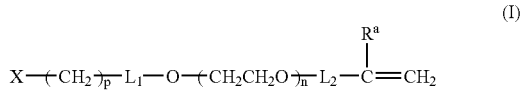

[in which X stands for hydrogen, —COOZ group (wherein Z standing for hydrogen or an organic group), —CHR¹R² (wherein R¹ and R² independently standing for $C_{1-6}$ alkyloxy, phenyloxy or phenyl-$C_{1-3}$ alkyloxy, or R¹ and R² together forming —OCHR'—CH₂O—, R' standing for hydrogen or $C_{1-6}$ alkyl) or —CH=O, $R^a$ stands for hydrogen or $C_{1-6}$ alkyl, $L_1$ stands for methylene or carbonyl, $L_2$ stands for carbonyl, $C_{1-3}$ alkylene or $C_{1-3}$ alkylphenylene, or X—(CH₂)$_p$-$L_1$-integrally stands for hydrogen or $C_{1-6}$ alkyl, n is an integer of 2–10,000, and p is an integer of 1–5] and a polymerization initiator; with (b) a comonomer represented by the formula II:

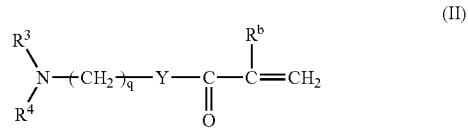

(in which $R^3$ and $R^4$ each independently stands for $C_{1-6}$ alkyl, $R^b$ stands for hydrogen or $C_{1-6}$ alkyl, Y stands for —O— or —NH—, and q is an integer of 2–6); and (c) a crosslinking agent having 2, 3, or more polymerizable unsaturated groups;

then heating the liquid mixture under stirring, to a temperature allowing initiation of the polymerization reaction; and continuing the reaction until said comonomer (b) and crosslinking agent (c) become no more detectable; using said macromonomer (a) and the comonomer (b) at a molar ratio ranging 1/400–, preferably 1/200–, in particular, 1/100–2/1, and using the crosslinking agent at a ratio of 0.1–25 mol % to the total amount of these monomers. Furthermore, this production method of the crosslinked polymer can be used to provide both the crosslinked polymer per se, and the polymer fine particles simultaneously.

The invention provides, still in addition, a method for producing polymer fine particles with semiconductor ultrafine particles fixed in their core parts, which comprises the steps of mixing an aqueous solution of said polymer fine particles with an aqueous solution of chloride of Group II B or III B element of the periodic table at such a ratio that the nitrogen atoms in said polymer fine particles become 1–20 molar times that of said element and stirring the mixture; and adding thereto an aqueous solution containing at least an equivalent amount to said chloride of an alkali metal salt of a Group VI B element to further continue the reaction; using the reactants at the molar ratio between the nitrogen content of the fine particles and the Group II B or III B element ranging 1:1–1:12. As another embodiment, the invention provides a method for producing polymer fine particles with gold ultrafine particles fixed in their core parts, which comprises adjusting pH of an aqueous solution of said polymer fine particles to about 6, separately preparing an aqueous solution of chloroauric acid and adjusting its pH to about 6, mixing the two aqueous solutions such that the nitrogen atoms in the polymer fine particles are 1–20 times the gold atoms in molar ratio, and stirring the mixture under the conditions sufficient to form gold fine particles and fix the same at core parts of said polymer fine particles.

DETAILED DESCRIPTION OF THE INVENTION

Hereinafter the present invention is explained more specifically.

Those crosslinked polymers following the invention are also referred to as three-dimensional polymers or network polymers, most of which are substantially insoluble in solvents including water, and form polymer fine particles following the present invention. Whereas, in water each molecule as a whole or the particles are solubilized by the action of the PEG segment present in said PEG macromonomer, to assume an appearance resembling a solution in the normal sense of the term. The term, solution, in this specification therefore encompasses the case wherein the solute polymer as a whole or the polymer fine particles are solubilized and the system assumes an appearance as if it were a solution.

Hence the crosslinked polymers can be present in such aqueous solutions as fine particles or beads, in solubilized or dispersed state. Such fine particles can be separated from the solution as solid particles by such means as centrifuge, filtration or the like. The fine particles of either forms are embodiments of the present invention.

Again as aforesaid, crosslinked polymers of the present invention can simultaneously form fine particles thereof or can be conveniently used for preparation of the fine particles. Whereas, so long as they have the above-described structural characteristics, the polymer fine particles of the present invention are not limited to those derived from the crosslinked polymers. Furthermore, the polymer fine particles following the present invention are clearly distinguishable from conventional fine particles such as those normally referred to as latex gel, in that their average particle size lies within a range of 30 nm–10 μm, preferably 50 nm–1 μm, when they are dispersed in purified water and subjected to a dynamic light scattering particle size analysis (DLS); and in that their average particle size as measured by DLS at pH 4 increases to 1.30–70.0 times that of the same particles as measured by DLS at pH 10.

Accordingly, the polymer fine particles are not limited by the kinds of monomers used for their preparation, so long as they meet the above construction requirements or have the structural characteristics or characteristic properties as above-described. For example, the group (linker) which links N,N-di-$C_{1-6}$ alkyl-substituted amino groups to polymer main chains is not limited to —$(CH_2)_q$—Y—CO— of the formula (II), but may be any so long as it is a linker of a chain length allowing the amino group to constitute a part of the core of the polymer fine particle. Specifically, the linker may be any that is formed of 1–10 atoms of carbon, nitrogen and oxygen. Whereas, the main chain is "formed of ethylenically unsaturated polymerizable groups" as aforesaid, i.e., formed of polymerizable vinyl groups.

The side chain whose hydrophilic group having a poly (ethylene glycol) segment is covalently bonded to the main chain may be a poly(ethylene glycol) chain bound to the main chain via an ester linkage or ether linkage, or may be one as described in, for example, WO 96/32434, WO 96/33233 or WO 97/06202, i.e., one in which one end of its poly(ethylene glycol) is modified with a certain functional group, with the other end bound to a hydrophobic polymer segment, the side chain being derived from an ethylenically unsaturated polymerizable group at the unbound end of said hydrophobic polymer segment. So long as the resulting polymer fine particles exhibit the characteristic properties specified in the present invention, they are included in the scope of polymer fine particles of the present invention. As a further specific explanation, the explanation of the crosslinked polymers given later is applicable.

Including above $C_{1-6}$ alkyl, alkyl group or alkyl moiety in alkyloxy group as referred to in the present specification signify straight chain or branched chain alkyl. Hence, as examples of $C_{1-6}$ alkyl and alkyl moiety in alkoxy, methyl, ethyl, n-propyl, iso-propyl, n-butyl, sec-butyl, tert-butyl, n-pentyl, iso-pentyl, n-hexyl, 2-methylpentyl, 3-methylpentyl and the like can be named. Of these, as the alkyl moiety of alkyloxy as $R^1$ and $R^2$ in the formula I and alkyl as $R^b$, $R^3$ and $R^4$ in the formula II, $C_{1-3}$ alkyl are particularly preferred.

Hence, examples of particularly preferred alkoxy group as $R^1$ and $R^2$ are methoxy, ethoxy, propoxy and isopropoxy. As other preferred $R^1$ and $R^2$, phenyloxy or phenyl $C_{1-3}$ alkyloxy, in particular, benzyloxy or phenethyloxy, can be named. While $R^1$ and $R^2$ may be the same or different, they are preferably the same. Or, $R^1$ and $R^2$ may together be an optionally $C_{1-6}$ alkyl-substituted 1,2-ethylenedioxy [—OCH (R')—CH$_2$O—: where R' is $C_{1-6}$ alkyl], preferably 1,2-ethylenedioxy, 1-methyl-1,2-ethylenedioxy, or 1-ethyl-1,2-ethylenedioxy.

The —CHR$^1$R$^2$ group (corresponding to acetalized or ketalized formyl group) formed of above-described groups can be readily converted to a formyl group (or aldehyde group) in which $R^1$ and $R^2$ together form oxy (═O), i.e., X represents —CH═O, by, for example, an acid treatment. Therefore, a crosslinked polymer having formyl groups (or aldehyde groups) or carboxyl groups bound to one end of the PEG chains can be provided through the steps of preparing a crosslinked polymer using a macromonomer of the formula (I) in which X is other than hydrogen or —CH═O group, and then treating the polymer with an acid (e.g., acetic acid).

$R^a$ and $R^b$ are preferably methyl or hydrogen independently of each other, and $R^3$ and $R^4$ are preferably methyl, ethyl or n-propyl, independently of each other.

L is carbonyl (═C═O), $C_{1-3}$ alkylene or $C_{1-3}$ alkylphenylene

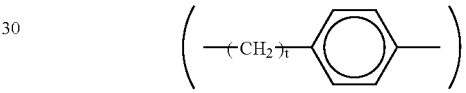

(wherein t is an integer of 1–3), preferably carbonyl, methylene or benzylene

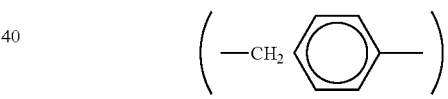

As n can be an integer of 2–10,000, the term "polymer" as used herein represents a concept including oligomer.

Hereinafter preparation of crosslinked polymers or formation of fine particles pertaining to preferred embodiments of polymer fine particles following the present invention are explained, it being understood that the polymer fine particles of the invention are not limited by the following descriptions.

Those macromonomers which can be used in the present invention can be prepared by versatile methods, referring to the structure represented by the formula I. They can be prepared by partially modifying terminals of commercial PEG's, by such means as subjecting them to, for example, dehydrohalogenation reaction using (meth)acrylic acid chloride, vinylbenzyl chloride or allyl chloride. Whereas, when prepared by the procedures referred to as living polymerization as described in patent reference 6, poly(ethylene glycol) or poly(oxyethylene) segment having one-peak molecular weight distribution can be obtained, by adjusting the use rate of ethylene oxide to the polymerization initiator used. Therefore, very narrow range distribution (monodispersion) can be realized within a range of n=2–10,000, preferred n being an integer of 10–200.

Whereas, p is an integer of 1–5, preferably 1–3.

The monomers represented by the formula II are aminoalkylamides or esters of (meth)acrylic acid, $R^b$, $R^3$ and $R^4$ therein having the definitions as presented earlier. Those particularly preferred are N,N-diethylaminoethyl methacrylate or methacrylamide, N,N-dimethylaminoethyl methacrylate or methacrylamide, and N,N-diethylaminopropyl methacrylate or methacrylamide; and acrylates or acrylamides corresponding to the foregoing.

The crosslinking agent (c) is a polyfunctional monomer having two or three, or more polymerizable unsaturated groups, which may be any that is copolymerizable with monomers of the formulae I and II and is capable of accomplishing the object of the present invention. Those versatile commercialized crosslinking agents can be used in their sold forms. Although not in limitative sense, preferred crosslinking agents can be expressed by a formula III:

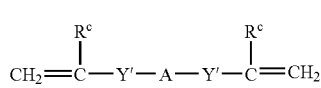

(III)

[in which $R^c$ stands for hydrogen or a $C_{1-6}$ alkyl; Y' stands for a valence bond, CO— or —NH—; and A stands for a phenylene —$(CH_2)_\gamma$— (where $\gamma$ is an integer of 1–4) or —$(OCH_2CH_2O)_s$— (wherein s is an integer of 1–4)].

More specifically, particularly favorable crosslinking agents are ethylene glycol di(meth)acrylate, diethylene glycol di(meth)acrylate, triethylene glycol di(meth)acrylate, divinylbenzene and N,N'-methylenebisacrylamide.

Crosslinked polymers according to the present invention may optionally comprise at least one, preferably only one, kind of recurring unit derived from diluent monomer(s) having polymerizable unsaturated group(s). Although not in limitative sense, as the diluent monomers styrene, methyl (meth)acrylate, butyl(meth)-acrylate, 2-ethylhexyl (meth) acrylate, (meth)acrylic acid amide, 2-hydroxyethyl methacrylate, isoprene and butadiene can be named. As can be understood from above-named examples, the terms "(meth) acrylate" and "(meth)acrylic acid" used in this specification signify, respectively, methacrylate or acrylate, and methacrylic acid or acrylic acid.

The macromonomer (a) (which forms the side chains (ii) of the polymer fine particles) and the comonomer (b) (which forms the side chains (i) of the polymer fine particles), which are indispensable for constructing preferred embodiments of crosslinked polymers or polymer fine particles, can be used at a molar ratio of 1/400–, preferably 1/200–, in particular 1/100–2/1. To the total amount of the macromonomer (a) and the comonomer (b), the crosslinking agent is used at a ratio of 0.1–25 mol %.

Copolymerization reaction of these monomers can be conducted under the conditions as will induce radical polymerization, e.g., using as the solvent water which may contain, where necessary, a water-miscible organic solvent such as methanol or ethanol, preferably water alone; and as the initiator potassium persulfate, sodium persulfate, ammonium persulfate, 4,4'-azobis-4-cyanovalerianic acid or the like; under heating where necessary. The reaction can be conveniently conducted with violent agitation of a mixed solution of the reactants in the state deaerated with inert gas (e.g., nitrogen, argon or the like). The reaction is continued until unreacted monomer disappears, as determined by, for example, analyzing an aliquot of the reaction mixture by means of gas chromatography. Thus, generally a crosslinked polymer is obtained in the form of fine particles (or beads). Sizes of such fine particles can be adjusted to about 30 nm, preferably 50 nm–about 1 μm, by selecting the use ratios of macromonomer (a), comonomer (b) and crosslinking agent (c) in the reaction, and by selecting the molecular weight of PEG in the macromonomer (a). The size can be adjusted, where necessary, to no less than 1 μm but no more than 10 μm. Hence the fine particles of the present invention can be referred to as nanospheres or microspheres. Furthermore, their particle sizes can also be adjusted by changing pH of the aqueous medium as aforesaid. Normally, fine particles of greater particle size can be formed by increasing the blend ratio of the comonomer, while density of the network can be adjusted by changing the use rate of the crosslinking agent. Where 2-hydroxyethyl methacrylate, (HEMA), for example, is concurrently used as a diluent monomer, water-solubility of the fine particles can be improved and, for example, when styrene is used concurrently, refractive index-improving property can be imparted to the fine particles.

Thus obtained fine particles (or nanospheres or microspheres) can be prepared with ease and good reproducibility. They are useful as unique functional materials depending on characteristic properties of PEG which mainly constitutes the shell domain and, where present, on utilization of functional groups at the PEG terminals. For example, for medical use, they can be used as carriers of mainly anionically charged drug, latex diagnosticum or cell separating medium.

The crosslinked polymer fine particles according to the invention can be provided as composite fine particles containing as fixed or encapsulated in the network structure and, furthermore, via the tertiary amine moiety, ultrafine particles of free electron metal such as gold, silver, copper or the like or, although not limited thereto, ultrafine particles of the following semiconductors. It is well known that ultrafine particles of gold, silver and the like are utilized as markers in biological assay systems and that nanocrystals or complexes thereof of a certain kind of semiconductors, for example, ZnS, CdSe, CdS, InP, InAs, CdTe, ZnSe, ZnTe and the like, are better fluorescent labels than organic dye (cf.e.g., Chan et al., *Science*, Vol. 281 (1998), 2016–2018; Mamedova et al., *Nano Lett.*, Vol. 1, (2001), 282–286; aforesaid Han et al.) Therefore, those composite fine particles according to the present invention are useful for biological assay systems or as quantum dots for other utilities.

The term, "ultrafine particles (or nanoparticles)" signify particles of all sizes which are capable of being fixed or encapsulated in the polymer fine particles of this invention. For example, gold or semiconductor ultrafine particles can have the diameters ranging 1–20 nm. By selecting, for example, the component constituting the semiconductor and/or particle size, these semiconductor ultrafine particles can provide polymer nano- or micro-spheres having different radiation wavelengths.

Fine particles or nano- or micro-spheres of such a crosslinked polymer containing as fixed or encapsulated in their core parts said metal or semiconductor ultrafine particles can be prepared by mixing and stirring said nano- or micro-spheres following the present invention with sol of said metal or semiconductor ultrafine particles in an aqueous medium. For fixing or encapsulating semiconductor ultrafine particles, a process comprising the following steps may be used: mixing and stirring an aqueous solution of, for example, a chloride of Group II B or III B element of the periodic table, with said aqueous solution of the microspheres to encapsulate the element in the microspheres; and then mixing and stirring the same with, for example, an aqueous solution of a salt of a Group VI B element of the periodic table with an alkali metal, or $H_2S$, to form a semiconductor within said nano- or micro-spheres in situ, and fix it there.

Moreover, for example, such semiconductor ultrafine particles as described in said patent reference 4 may be mixed and stirred with an aqueous solution of said microspheres; or the ultrafine particles may be fixed or encapsulated in fine particles of a crosslinked polymer produced, by causing said semiconductor ultrafine particles to be concurrently present in the reaction liquid at any one of the stages for preparing the crosslinked polymer of the present invention. While the use ratio of the semiconductor to the crosslinked polymer or polymer fine particles is preferably so adjusted that the nitrogen atoms in said polymer fine particles are 1–20 molar times the semiconductor molecules, the use ratio is not limited thereto.

Fixing or encapsulation of ultrafine particles of free electron metal, e.g., gold, in said microspheres or polymer fine particles can be effected by such processes following the above descriptions about that of semiconductor ultrafine particles. However, when a gold compound such as chloroauric acid is used, fixing of gold particles in polymer fine particles can be efficiently carried out by the steps of, for example, adjusting pH of an aqueous solution of the polymer fine particles to about 6; separately preparing an aqueous solution of chloroauric acid and adjusting its pH to about 6; and stirring the two aqueous solutions together under the conditions sufficient to form gold fine particles and for the formed particles to be fixed in the core domains of the polymer fine particles. Preferably the use ratio of the metal to the crosslinked polymer or polymer fine particles is so adjusted that the nitrogen atoms in said polymer fine particles should amount to 1–20 molar times of the metal atoms, but this is not limitative.

In above fixing or encapsulating processes, concentration of polymer fine particles; or that of a semiconductor or its precursor material, or that of gold or its precursor material in the treating liquids are not critical, so long as the treating liquids can be mechanically stirred. Where necessary, skilled artisans will be able to determine the optimum concentration in each occasion by carrying out a small scale experiment referring to later appearing working Examples. The treating temperature can be ambient temperature, but the system can be heated or cooled within the range not detrimental to the fixation or encapsulation in each occasion.

These conditions may also be used in the occasion of polymerization to make the crosslinked polymers.

The patent or application file contains at least one drawing executed in color. Copies of this patent or patent application publication with color drawing(s) will be provided by the Office upon request and payment of the necessary fee.

BRIEF DESCRIPTION OF DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
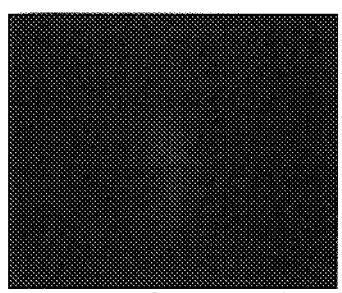
FIG. 1 shows photographs in place of drawings showing the result of fluorescence observation with laser fine particles' fluorescence detector of the CdS-fixed polymer fine particles (Example 7).
Figure 1:
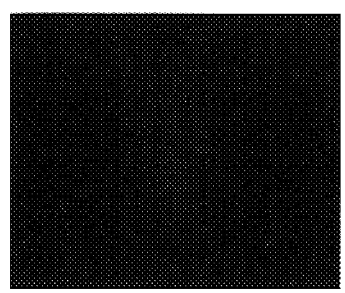
Figure 1:
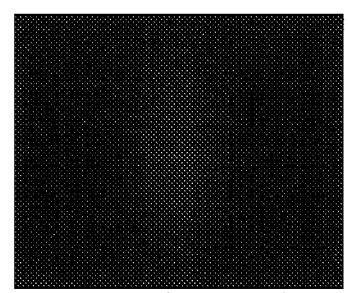
Figure 1:
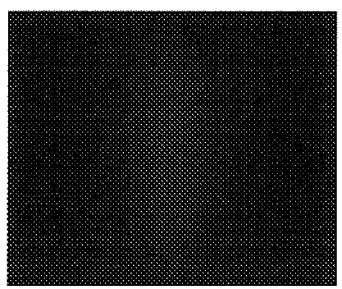
Figure 1:
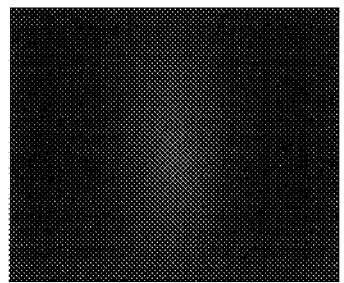
Figure 1:
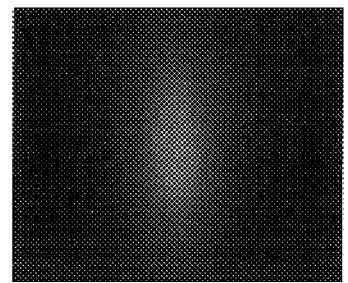

Hereinafter the invention is more specifically explained referring to working Examples which, however, are not intended to thereby limit the present invention.

<Significations of Abbreviations Used in the Examples>
The abbreviations stand for the following, respectively.
Component (a): macromonomer
m-PEGMA: polyethylene glycol macromonomer 1: α-methoxy-ω-methacryloyl-polyethylene glycol
c-PEGVB: polyethylene glycol macromonomer 2: α-vinylbenzyl-ω-carboxyl-polyethylene glycol
Component (b): comonomer
DEAEMA: N,N-diethylaminoethyl methacrylate (monomer)
Component (c): crosslinking agent
EDMA: ethylene glycol dimethacrylate (crosslinking agent)
DVB: divinylbenzene
KPS: potassium persulfate (polymerization initiator)
Fine particles (nanospheres): PEG-p(DEAEMA-EDMA), CdS-encapsulating nanospheres: PEG-p(DEAEMA-EDMA)-CdS <Analyzing Machineries and Tools Used in the Examples>
GSC (gas chromatograph): GC5890 SERIES II (Hewlett-Packard)
DLS (dynamic light scattering particle size analyzer): DLS-7000 (Otsuka Electronics Co.)
Elementary analysis measuring apparatus: (Parkin Elmer)
Laser fine particle fluorescence detecting device): ZEECOM (Microtech Co., Ltd.)
Transmission electronmicroscope: TEM (Hitachi HD 2000)

EXAMPLE 1

Synthesis of m-PEGMA-p(DEAEMA-EDMA)-400

Into a reaction vessel 12 g of α-methoxy-ω-methacryloyl polyethylene glycol [number average molecular weight of m-PEGMA (polyethylene glycol macromonomer) was 5,000], 449 mg of KPS and 900 ml of water were fed and dissolved under stirring. After deaerating this reaction vessel with an aspirator, the atmosphere was argon-substituted. Another vessel was argon-substituted, and into which 30 g of DEAEMA and 327 mg of EDMA were fed with a syringe and stirred. Further, said DEAEMA/EDMA mixed solution was added to the polyethylene glycol macromonomer/KPS aqueous solution with a syringe, stirred for 30 minutes at room temperature, and reacted for 24 hours under an elevated temperature of 60° C. After said 24 hours, the reaction mixture was given a GC measurement and disappearance of unreacted DEAEMA and EDMA was confirmed. Thus obtained polymerization product was filtered to be removed of insoluble matters, followed by sedimentation of the soluble component by centrifugal operation. The soluble component was dispersed in purified water, to provide an aqueous solution of m-PEGMA-p(DEAEMA-EDMA)-400 nanospheres.

Particle diameters and particle size distribution of so obtained nanospheres were measured with the DLS identified in the above. Also 1 ml of the nanospheres' aqueous solution was lyophilized to calculate the polymer content of the aqueous solution. The lyophilized product further was given an elementary analysis to determine the nitrogen content in the dry polymer. The results were as shown in the following Table 1.

EXAMPLE 2

Synthesis of m-PEGMA-p(DEAEMA-EDMA)-300

Operations same as in Example 1 were repeated except that 6.21 g of m-PEGMA (number average molecular weight was 5,000), 14.71 g of DEAEMA, 150 mg of EDMA, 450 ml of water and 204 mg of KPS were used, to produce an aqueous solution of m-PEGMA-p(DEAEMA-EDMA)-300 nanospheres.

Thus obtained nanospheres were evaluated similarly to Example 1. The results were as shown in the following Table 1.

EXAMPLE 3

Synthesis of c-PEGVB-p(DEAEMA-EDMA)-50

In a reaction vessel 0.25 g of α-vinylbenzyl-ω-carboxylpolyethylene glycol (number average molecular weight of the polyethylene glycol macromonomer was 2,000), 7.7 mg of KPS and 15 ml of water were fed and dissolved under stirring. The reaction vessel was deaerated with an aspirator. Another vessel was argon-substituted, and into which 0.50 g of DEAEMA and 5.6 mg of EDMA were fed with a syringe and stirred. Further, said DEAEMA/EDMA mixed solution was added to the polyethylene glycol macromonomer/KPS aqueous solution with a syringe, stirred for 30 minutes at room temperature, and reacted for 24 hours under an elevated temperature of 60° C. After said 24 hours, the reaction mixture was given a GC measurement and disappearance of unreacted DEAEMA and EDMA was confirmed. Thus obtained polymerization product was filtered to be removed of insoluble matters to provide an aqueous solution of c-PEGVB-p(DEAEMA-EDMA)-50 nanospheres.

Thus obtained nanospheres were evaluated similarly to Example 1. The results were as shown in the following Table 1.

EXAMPLE 4

Preparation of m-PEGMA-p(DEAEMA-EDMA)-400-CdS

Using the m-PEGMA-p(DEAEMA-EDMA)-400 which was prepared in Example 1, m-PEGMA-p(DEAEMA-EDMA)-CdS was prepared, varying the molar ratio of the nitrogen content of the nanospheres to the Cd ion within a range of 1:1–1:12. The preparation conditions were as given in the following Table 2.

To an m-PEGMA-p(DEAEMA-EDMA) nanospheres' aqueous solution (4 ml) which had been diluted to a prescribed concentration, 1 ml of an aqueous solution of $1.0 \times 10^{-3}$ M cadmium chloride ($1.0 \times 10^{-5}$ mol) was added, followed by stirring for a short time. Then 1 ml of an aqueous solution of $1.0 \times 10^{-3}$ M sodium sulfide nonahydrate ($1.0 \times 10^{-5}$ mol) was slowly added thereto dropwisely at room temperature. After an hour's reaction, PEG-p(DEAEMA-EDMA)-400-CdS was obtained, whose appearance was as shown in Table 3.

EXAMPLE 5

Preparation of m-PEGMA-p(DEAEMA-EDMA)-300-CdS

Operations similar to those in Example 4 were repeated except that the m-PEGMA-p(DEAEMA-EDMA)-300 as obtained in Example 2 was used, to provide m-PEGMA-p(DEAEMA-EDMA)-300-CdS. Their preparation conditions were as shown in Table 2. The appearances of so obtained PEG-p(DEAEMA-EDMA)-300-CdS was as shown in Table 3.

EXAMPLE 6

Preparation of c-PEGVB-p(DEAEMA-EDMA)-50-CdS

Operations similar to those in Example 4 were repeated except that the c-PEGVB-p(DEAEMA-EDMA)-50 as obtained in Example 3 was used, to provide c-PEGVB-p(DEAEMA-EDMA)-50-CdS. Their preparation conditions were as shown in Table 2. The appearance of so obtained c-PEGVB-p(DEAEMA-EDMA)-50-CdS was as shown in Table 3.

TABLE 1

Analyses Results of m-PEGMA-p(DEAEMA-EDMA) and c-PEGVB-p(DEAEMA-EDMA)

| Sample | Average Particle Size (nm) | $\mu/\Gamma^2$ | Polymer Content (%) | N Content (measured) (%) | N Content (calculated) (%) |
|---|---|---|---|---|---|
| m-PEGMA-p(DEAEMA-EDMA)-400 | 416.0 | $6.129 \times 10^{-2}$ | 6.58 | 7.27 | 5.36 |
| m-PEGMA-p(DEAEMA-EDMA)-300 | 279.1 | $2.968 \times 10^{-2}$ | 2.90 | 6.43 | 5.28 |
| c-PEGVB-p(DEAEMA-EDMA)-50 | 55.2 | $9.400 \times 10^{-2}$ | 1.38 | — | 5.00 |

TABLE 2

Preparation Conditions of m-PEGMA-p(DEAEMA-EDMA)-CdS and c-PEGVB-p(DEAEMA-EDMA)-CdS

| Run No. | nanospheres | $CdCl_2$ | $Na_2S.9H_2O$ | N:Cd (molar ratio) | CdS concentration |
|---|---|---|---|---|---|
| 1 | m-PEGMA-p(DEAEMA-EDMA)-400 | $1.0 \times 10^{-5}$ mol | $1.0 \times 10^{-5}$ mol | 1:1 | $1.67 \times 10^{-3}$ M |
| 2 | | ↑ | ↑ | 1:2 | ↑ |
| 3 | | ↑ | ↑ | 1:5 | ↑ |
| 4 | | ↑ | ↑ | 1:8 | ↑ |
| 5 | | ↑ | ↑ | 1:12 | ↑ |
| 6 | m-PEGMA-p(DEAEMA-EDMA)-300 | ↑ | ↑ | 1:1 | ↑ |
| 7 | | ↑ | ↑ | 1:2 | ↑ |
| 8 | | ↑ | ↑ | 1:5 | ↑ |
| 9 | | ↑ | ↑ | 1:8 | ↑ |
| 10 | | ↑ | ↑ | 1:12 | ↑ |
| 11 | c-PEGVB-p(DEAEMA-EDMA)-50 | ↑ | ↑ | 1:1 | ↑ |
| 12 | | ↑ | ↑ | 1:2 | ↑ |
| 13 | | ↑ | ↑ | 1:5 | ↑ |
| 14 | | ↑ | ↑ | 1:8 | ↑ |
| 15 | | ↑ | ↑ | 1:12 | ↑ |

TABLE 3

Appearance of m-PEGMA-p(DEAEMA-EDMA)-CdS, and c-PEGVB-p(DEAEMA-EDMA)-CdS

| Run No. | Precipitate | Supernatant |
|---|---|---|
| 1 | Yes | Water-transparent |
| 2 | ↑ | ↑ |
| 3 | ↑ | ↑ |
| 4 | ↑ | ↑ |
| 5 | ↑ | ↑ |
| 6 | ↑ | ↑ |
| 7 | ↑ | Yellow solution |
| 8 | No | ↑ |
| 9 | ↑ | ↑ |
| 10 | ↑ | ↑ |
| 11 | ↑ | ↑ |
| 12 | ↑ | ↑ |
| 13 | ↑ | ↑ |
| 14 | ↑ | ↑ |
| 15 | ↑ | ↑ |

EXAMPLE 7

Fluorescence Observation with Laser Fine Particle Fluorescence Detection Device

Of the m-PEGMA-p(DEAEMA-EDMA)-CdS and c-PEGVB-p(DEAEMA-EDMA)-CdS as obtained in Examples 4–6, those of Run Nos. 10(Cd: N=1:12), 11(Cd: N=1:1), 12(Cd: N=1:2), 13(Cd: N=1:13), 14(Cd: N=1:8) and 15(Cd: N=1:12) were given fluorescence observation using Laser Fine Particles Fluorescence Detection Device manufactured by Microtech Co., Ltd. Whereupon it was confirmed that all of the PEG-p(DEAEMA-EDMA)-CdS as stably solubilized in water had fluorescent property (cf. FIG. 1).

EXAMPLE 8

Auto-Reduction Process of Gold Ions in c-PEGVB-DEAEMA Gel Nanoparticles (Experimental Conditions)

Figure 2:
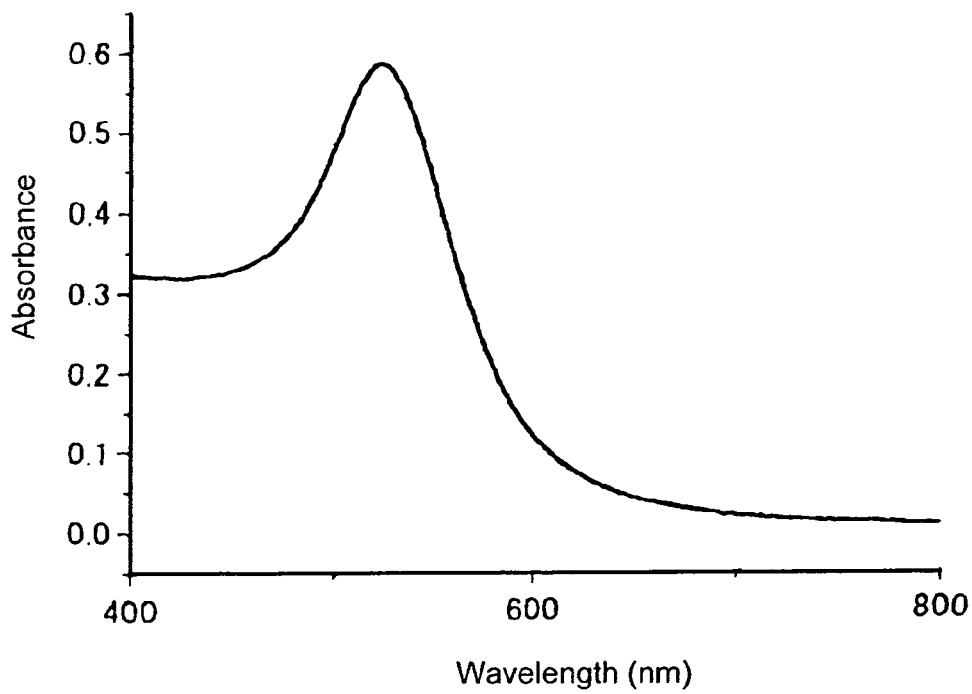
FIG. 2 is a UV-vis spectrogram of the product of Example 8, in which λ max=522.5 nm.

An aqueous solution of gel particles (average particle size: 120 nm) which were prepared under the condition of: c-PEGVB (number average molecular weight=1800): DEAEMA=1:4 (wt/wt), was lyophilized and concentration by weight was determined, which was 30.16 mg/ml. One(1) ml of this aqueous gel particle solution was measured out, diluted to 5 times with ultrapure water, and its pH was adjusted to 6. From an aqueous solution of 2.5 mg/ml of chloroauric acid tetrahydrate, 1 ml was measured out, its pH was adjusted to 6 and added to said aqueous gel particle solution under violent agitation. The agitation was continued for one day, to reduce gold ions. The resultant red-colored solution was diluted to 5 times and given a UV-vis spectral measurement. Thus obtained spectrogram was as shown in FIG. 2.

EXAMPLE 9

Synthesis of c-PEGVB-p(DEAEMA-EDMA)

In synthesizing nanospheres, weight ratio of polyethylene glycol macromonomer, c-PEGVB, and diethylaminoethyl methacrylate, DEAEMA, was varied within a range of 1/0.5–1/100. Thus plural c-PEGVB-p(DEAEMA-EDMA) were synthesized (Run Nos. 1–7). The feed amounts of the respective components were: 0.75 g of c-PEGVB and DEAEMA as combined, 1 mol % of the combined amount of EDMA, 1 mol % of the total amount (c-PEGVB+DEAEMA+EDMA) of KPS and 15 ml of water. The conditions of the syntheses were as shown in the following Table 4.

TABLE 4

Synthesizing Conditions of c-PEGVB-p(DEAEMA-EDMA)

| Run No. | c-PEGVB/DEAEMA weight ratio | c-PEGVB/DEAEMA molar ratio | Amount Added (mg) c-PEGVB | DEAEMA | EDMA | KPS |
|---|---|---|---|---|---|---|
| 1 | 1/0.5 | 1/4.8 | 500 | 250 | 3.2 | 4.5 |
| 2 | 1/1 | 1/9.6 | 375 | 375 | 4.4 | 6.1 |
| 3 | 1/2 | 1/19 | 250 | 500 | 5.6 | 7.7 |
| 4 | 1/4 | 1/39 | 150 | 600 | 6.6 | 9.1 |
| 5 | 1/8 | 1/78 | 83 | 667 | 6.9 | 9.9 |
| 6 | 1/50 | 1/486 | 15 | 785 | 7.9 | 10.9 |
| 7 | 1/100 | 1/971 | 7 | 743 | 8.0 | 11.0 |

Into a reaction vessel 0.15 g of α-vinylbenzyl-ω-carboxyl-polyethylene glycol (number average molecular weight of the polyethylene glycol macromonomer was 1800), 9.1 mg of KPS and 15 ml of water were fed and dissolved under stirring. After deaerating this reaction vessel with aspirator, 6.6 μl of EDMA and 650 μl of DEAEMA were added with syringe into the polyethylene glycol macromonomer/KPS aqueous solution, followed by 30 minutes' stirring at room temperature, heating to 60° C. and 24 hours' stirring. After said reaction for 24 hours, the reaction mixture was given a GC measurement and disappearance of unreacted DEAEMA and EDMA was confirmed. Removing insoluble matters from the resulting polymerization product by filtration, an aqueous solution of c-PEGVB-p(DEAEMA-EDMA) nanospheres was obtained.

Particle diameters and particle size distribution of the nanospheres obtained under the respective synthesizing conditions were measured with DLS. The results were as shown in the following Table 5.

TABLE 5

Synthesized c-PEGVB-p(DEAEMA-EDMA)

| Run No. | Average particle size (nm) | $\mu/\Gamma^2$ |
|---|---|---|
| 1 | 49.5 | 0.230 |
| 2 | 46.5 | 0.140 |
| 3 | 55.2 | 0.0940 |
| 4 | 62.9 | 0.0438 |
| 5 | 82.3 | 0.0881 |
| 6 | 196 | 0.0926 |
| 7 | 341 | 0.0206 |

EXAMPLE 10

Synthesis of c-PEGVB-p(DEAEMA-DVB)

In synthesizing the nanospheres, molecular weight of the polyethylene glycol macromonomer, c-PEGVB, was varied for each run, within a range of 1800–7300 to synthesize c-PEGVB-p(DEAEMA-DVB) (Run Nos. 1–3). The feed amounts of the respective components were: 0.75 g of c-PEGVB and DEAEMA as combined, 1 mol % of the combined amount of DVB, 1 mol % of the total amount (c-PEGVB+DEAEMA+DVB) of KPS and 15 ml of water. The conditions of the syntheses were as shown in the following Table 6.

TABLE 6

Synthesizing Conditions of c-PEGVB-p(DEAEMA-EDMA)

| Run No. | PEG Molecular Weight | c-PEGVB/DEAEMA molar ratio | c-PEGVB/DEAEMA weight ratio | Amount added (mg) c-PEGVB | DEAEMA | DVB | KPS |
|---|---|---|---|---|---|---|---|
| 1 | 1800 | 1/39 | 1/4 | 150 | 600 | 4.3 | 9.1 |
| 2 | 4200 | 1/39 | 1/0.882 | 399 | 351 | 2.6 | 5.4 |
| 3 | 7300 | 1/39 | 1/0.255 | 598 | 152 | 1.2 | 1.2 |

Into a reaction vessel 0.15 g of α-vinylbenzyl-ω-carboxyl-polyethylene glycol (number average molecular weight of the polyethylene glycol macromonomer was 1800), 9.1 mg of KPS and 15 ml of water were fed and dissolved under stirring. After deaerating this reaction vessel with aspirator, 4.8 μl of DVB and 650 μl of DEAEMA were added with syringe into the polyethylene glycol macromonomer/KPS aqueous solution, followed by 30 minutes' stirring at room temperature, heating to 60° C. and 24 hours' stirring. After said reaction for 24 hours, the reaction mixture was given a GC measurement and disappearance of unreacted DEAEMA and DVB was confirmed. Removing insoluble matters from the resulting polymerization product by filtration, an aqueous solution of c-PEGVB-p(DEAEMA-DVB) nanospheres was obtained.

Thus obtained nanospheres were given evaluations similar to those in Example 9, with the results as shown in the following Table 7.

TABLE 7

Result of c-PEGVB-p(DEAEMA-EDMA) Syntheses

| Run No. | Average particle size (nm) | $\mu/\Gamma^2$ |
|---|---|---|
| 1 | 65.0 | 0.064 |
| 2 | 52.0 | 0.078 |
| 3 | 56.0 | 0.093 |

EXAMPLE 11

Treatment of Polymer Fine Particles in Solutions of Differing pH

This Example demonstrates that diameters of polymer fine particles of the present invention are pH-responsive.

Using the c-PEGVB-p(DEAEMA-EDMA)-63 (Run No. 4) as synthesized in Example 9, their particle diameter changes in aqueous solutions of different pH values were measured with DLS.

To 3 ml each of aqueous c-PEGVB-p(DEAEMA-EDMA) nanosphere solution diluted to the prescribed concentration (0.5 mg/ml), $1.0 \times 10^{-2}$N-HCl or $1.0 \times 10^{-2}$N-NaOH aqueous solution was added to change pH of the system within a range of 3–12. Resulting particle diameters were measured with DLS. The results were as shown in Table 8.

TABLE 8

Nanoshere Diameters at Respective pH

| pH | Average particle size (nm) | $\mu/\Gamma^2$ |
|---|---|---|
| 3.4 | 142 | 0.041 |
| 3.9 | 143 | 0.050 |
| 5.0 | 143 | 0.067 |
| 5.7 | 139 | 0.052 |
| 6.4 | 107 | 0.055 |
| 6.6 | 95.8 | 0.063 |
| 6.7 | 80.0 | 0.052 |
| 6.9 | 67.0 | 0.085 |
| 7.0 | 65.2 | 0.076 |
| 9.3 | 68.1 | 0.074 |
| 10.3 | 67.9 | 0.084 |
| 11.2 | 67.5 | 0.091 |
| 12.1 | 65.4 | 0.085 |

EXAMPLE 12

Preparation of Polymer Fine Particles with Varied Use Rate of Crosslinking Agent DVB This Example demonstrates particle diameters and volume swellability of product fine particles can be controlled by varying use rate of crosslinking agent.

Using the system similar to that for making c-PEGVB-p(DEAEMA-DVB)-18 as synthesized in Example 10 (Run No. 1), DVB concentration was varied and its influence on degree of volumetric swelling as calculated from the particle diameters at pH 4 and those at pH 10 was evaluated.

Nanospheres were synthesized by the method same to c-PEGVB-p(DEAEMA-DVB)-18 (Run No. 1) except that the added amount of DVB alone was changed within a range of 0.1 mol %–25 mol %. Each product solution was diluted to a concentration of 0.5 mg/ml, and their pH was changed to 4 and 10 by adding thereto $1.0 \times 10^{-2}$ N-HCl or $1.0 \times 10^{-2}$ N-NaOH aqueous solution. Particle sizes under the respective conditions were measured with DLS. The results were as shown in Table 9.

TABLE 9

DVB Concentration vs. Particle Sizes and Degree of Swelling at pH4 and pH 10

| Run No. | DVB concentration (mol %) | Average particle size (nm) pH 10 | Average particle size (nm) pH 4 | Degree of volumetric swelling VpH 4/VpH 10 |
|---|---|---|---|---|
| 1 | 0.1 | 261.1 | 63.5 | 69.5 |
| 2 | 0.3 | 241.2 | 60.8 | 62.4 |
| 3* | 1 | 166.4 | 62.4 | 19.0 |
| 4 | 3 | 127.6 | 56.6 | 11.5 |
| 5 | 10 | 95.6 | 57.3 | 4.64 |
| 6 | 25 | 94.3 | 85.9 | 1.32 |

*Run No. 3 is c-PEGVB-p(DEAEMA-DVB)-18 (Run No. 1)

EXAMPLE 13

Auto-Reduction of Gold Ions in c-PEGVB-p(DEAEMA-DVB) Gel Nanoparticles

A 50 ml glass reaction vessel equipped with a three-way cork, which was charged with 0.15 g (0.08 mmol) of c-PEGVB (number average molecular weight, 1800) and 9.1 mg (0.03 mmol) of an initiator KPS, was evacuated for 15 minutes, and then argon (Ar) was hermetically supplied thereinto. Repeating three cycles of these operations, the inside of the reaction vessel was substituted with Ar atmosphere. Then deaerated distilled water was added as the polymerization solvent. Further 48 μl (0.03 mmol) of a crosslinking agent DVB and 650 μl (3.2 mmols) of a comonomer DEAEMA were added, and temperature of the reaction liquid was raised to 60° C. with a hot water bath to initiate the polymerization.

Figure 3:
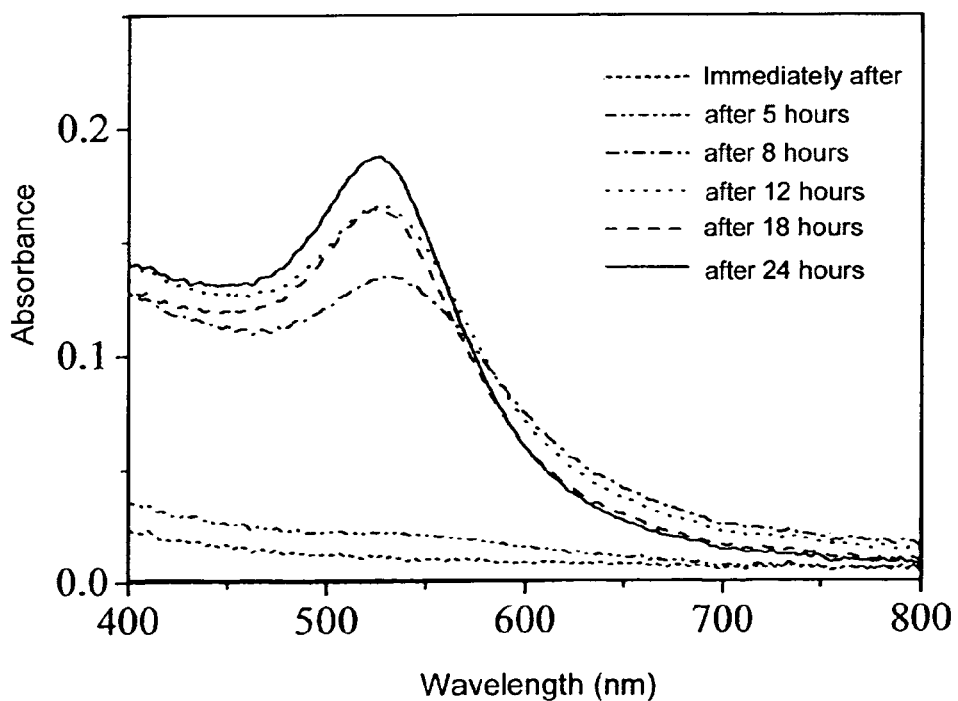
FIG. 3 is a spectrogram showing the changes with time in the UV-vis spectrum to illustrate progress in gold ion reduction in the polymer fine particle gel in Example 13.

After the crosslinking agent and comonomer became no more detectable by GC measurement, 30 μl of the reaction solution (50 mg/ml) was measured out and added to 3 ml of distilled water (0.5 mg/ml) and measured with DLS (particle size 60 nm). Thus obtained particles were purified by ultracentrifugation (350,000×g, 20° C., 15 min.×1). From an aqueous solution of the gel particles prepared from the purified particles (3.34 mg/ml), 2 ml was measured out and its pH was adjusted to 6 with hydrochloric acid. Separately, pH of an aqueous solution of chloroauric acid as dissolved in ultrapure water (1.43 mg/ml) was adjusted to 6 with sodium hydroxide. These aqueous solutions were mixed in a reaction vessel and violently stirred for a day at room temperature under open atmosphere, to provide gold fine particles through the reduction by the nanopolymer fine particle gel. The blend ratio of amino group and gold ion in this solution was adjusted to make Au: N=1:8. Thus obtained red-colored solution was diluted to thirtyfold and by its ultraviolet visible light absorption (UV-vis spectrum) measurement, reduction of gold ions and formation of gold fine particles were evaluated. The results were as shown in FIG. 3.

Figure 4:
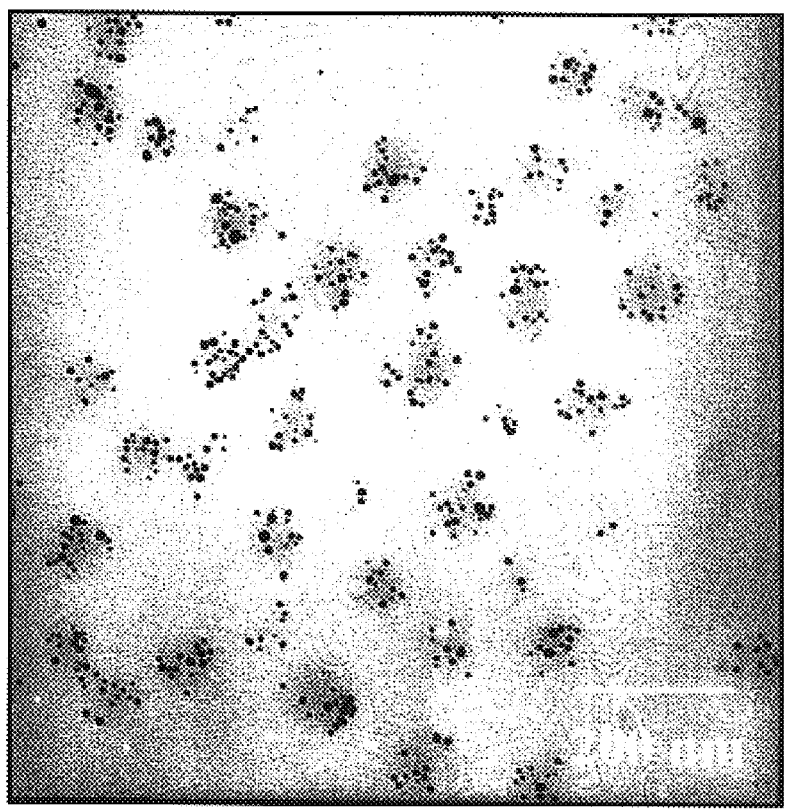
FIG. 4 is a transmission electronmicorgraph in place of a drawing, showing shapes of the gold ultrafine particles formed in Example 13.

Thus obtained nanogel-reduced colloidal gold was diluted to one-hundredfold with ultrapure water and casted on a collodion film-applied copper grid for TEM observation with a platinum loop, dried in a dessicator and observed with TEM. Its electronmicrograph is shown as FIG. 4, in place of a drawing showing the result. Upon the image analysis, formation of gold fine particles having an average particle size of 6.1 nm and degree of polydispersion of 1.15 was confirmed.

Figure 5:
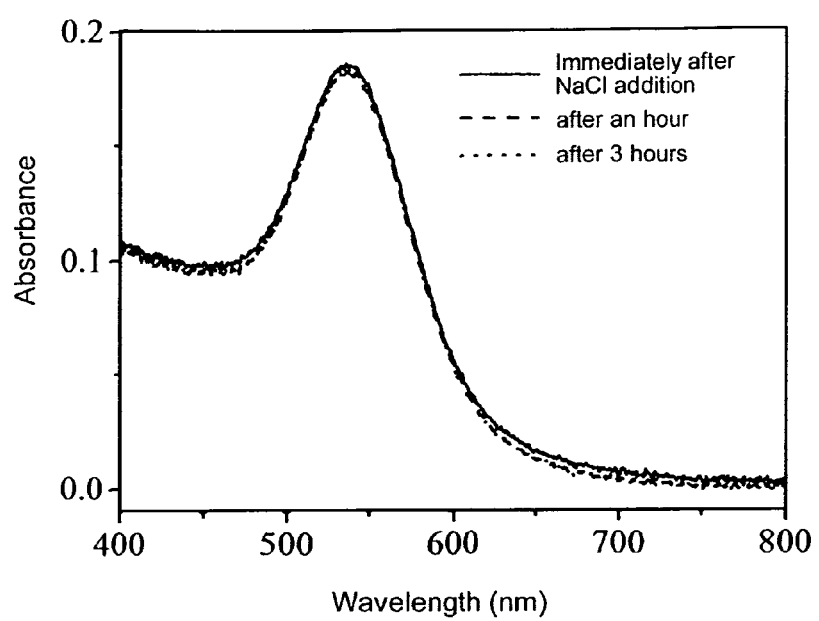
FIG. 5 is a graph demonstrating dispersion stability of the gold ultrafine particles-fixed or encapsulating polymer fine particles obtained in Example 13, in an environment of high salt concentration.

The reduced colloidal gold gel (gold-fixed polymer fine particles) solution as obtained in the above was diluted to fortyfold with ultrapure water. To 800 μl of said diluted solution, 200 μl of 5.0 M-NaCl aqueous solution was added and its UV-vis spectral change in 1.0 M-NaCl environment (high salt concentration environment as would readily aggregate colloidal gold obtained through citric acid reduction) with time was observed. The result was as shown in FIG. 5. From the same figure, it is verified that the polymer fine particles containing gold ultrafine particles as fixed or encapsulated therein keep being stably dispersed in such a high salt concentration environment as above.

INDUSTRIAL APPLICABILITY

According to the present invention, polymer fine particles, crosslinked polymers, and further gold or semiconductor-encapsulating polymer fine particles which are stable in aqueous dispersion systems are provided, which are useful as carriers for in vivo delivery of drug, in particular, medicines, and also as markers or quantum dots in the field of bioassays. Accordingly, the present invention is utilizable in the trade of manufacturing fine polymers, that of manufacturing medical preparations, and the like.

The invention claimed is:

1. Polymer fine particles derived from a crosslinked polymer having main chains formed of ethylenically unsaturated polymerizable groups and crosslinkages between said main chains, which are characterized in that
said main chain comprises (i) side chains each of N, N-di-$C_{1-6}$ alkyl-substituted amino group covalently bonded to said main chain via a linker formed of 1–10 atoms, and (ii) side chains each of a hydrophilic group having a poly(ethylene glycol) segment which is covalently bonded to said main chain, independently of each other;
the polymer fine particles thus forming core-shell type fine particles when solubilized or dispersed in an aqueous medium, said side chains (i) and the main chains chiefly forming the core parts and the side chains (ii) chiefly forming the shell parts.

2. The polymer fine particles according to claim 1, which have an average particle size lying within a range of 30 nm–10 μm, when they are dispersed in purified water and subjected to a dynamic light scattering particle size analysis (DLS); their average particle size as measured by DLS at pH 4 increasing to 1.30–70.0 times that of the same particles as measured by DLS at pH 10.

3. The polymer fine particles according to claim 1, in which the main chains covalently bonded with the side chains (ii) are derived from a poly(ethylene glycol) macromonomer represented by a formula I:

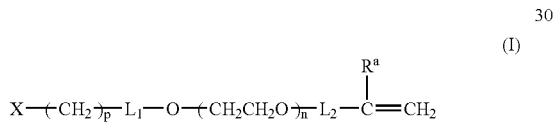

(I)

[in which X stands for hydrogen, —COOZ group (wherein Z standing for hydrogen or an organic group), —CHR$^1$R$^2$ (wherein R$^1$ and R$^2$ independently standing for $C_{1-6}$ alkyloxy, phenyloxy or phenyl-$C_{1-3}$ alkyloxy, or R$^1$ and R$^2$ together forming —OCHR'—CH$_2$O—, R' standing for hydrogen or $C_{1-6}$ alkyl) or —CH=O,
R$^a$ stands for hydrogen or $C_{1-6}$ alkyl,
L$_1$ stands for methylene or carbonyl,
L$_2$ stands for carbonyl, $C_{1-3}$ alkylene or $C_{1-3}$ alkylphenylene, or X—(CH$_2$)$_p$-L$_1$-integrally stands for hydrogen or $C_{1-6}$ alkyl,
n is an integer of 2–10,000, and p is an integer of 1–5]; and
the side chains (i) are derived from a comonomer represented by a formula II:

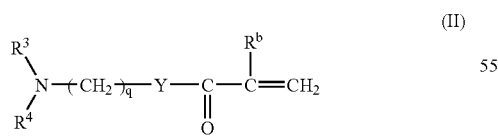

(II)

(in which R$^3$ and R$^4$ each independently stands for $C_{1-6}$ alkyl, R$^b$ stands for hydrogen or $C_{1-6}$ alkyl, Y stands for —O— or —NH—, and q is an integer of 2–6);
said polymer fine particles optionally further containing side chains derived from a diluent monomer.

4. The polymer fine particles according to claim 3, which do not contain any side chains derived from a diluent monomer.

5. The polymer fine particles according to claim 3, in which the crosslinkages are derived from a crosslinking agent expressed by a formula III:

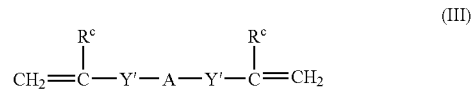

(III)

[in which R$^c$ stands for hydrogen or $C_{1-6}$ alkyl; Y' stands for a valence bond, carbonyl or —NH—; and A stands for phenylene, —(CH$_2$)$_\gamma$— (where γ is an integer of 1–4) or —(OCH$_2$CH$_2$O)$_s$— (wherein s is an integer of 1–4)].

6. The polymer fine particles according to claim 1, in which the monomer deriving the side chains (i) and the monomer deriving the side chains (ii) are present at a molar ratio ranging between 1/2 and 400/1, and the crosslinking agent is present at a ratio of 0.1–25 mol % to the total amount of the monomer (i) and monomer (ii).

7. The polymer fine particles according to claim 1, in which the main chains covalently bonded with the side chains (ii) are derived from a poly(ethylene glycol) macromonomer represented by a formula I:

(I)

[in which X stands for hydrogen, —COOZ group (wherein Z standing for hydrogen or an organic group), —CHR$^1$R$^2$ (wherein R$^1$ and R$^2$ independently standing for $C_{1-6}$ alkyloxy, phenyloxy or phenyl-$C_{1-3}$ alkyloxy, or R$^1$ and R$^2$ together forming —OCHR'—CH$_2$O—, R' standing for hydrogen or $C_{1-6}$ alkyl) or —CH=O,
R$^a$ stands for hydrogen or $C_{1-6}$ alkyl,
L$_1$ stands for methylene or carbonyl,
L$_2$ stands for carbonyl, $C_{1-3}$ alkylene or $C_{1-3}$ alkylphenylene, or X—(CH$_2$)$_p$-L$_1$-integrally stands for hydrogen or $C_{1-6}$ alkyl,
n is an integer of 2–10,000, and p is an integer of 1–5]; and
the side chains (i) are derived from a comonomer represented by a formula II:

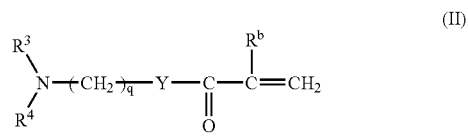

(II)

(in which R$^3$ and R$^4$ each independently stands for $C_{1-6}$ alkyl, R$^b$ stands for hydrogen or $C_{1-6}$ alkyl, Y stands for —O— or —NH—, and q is an integer of 2–6);
said polymer fine particles optionally further containing side chains derived from a diluent monomer; and the crosslinkages are derived from a crosslinking agent expressed by a formula III:

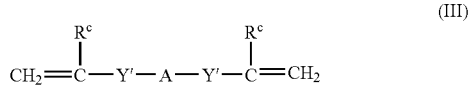

(III)

[in which $R^c$ stands for hydrogen or $C_{1-6}$ alkyl; Y' stands for a valence bond, carbonyl or —NH—; and A stands for phenylene, —$(CH_2)_\gamma$— (where $\gamma$ is an integer of 1–4) or —$(OCH_2CH_2O)_s$— (wherein s is an integer of 1–4)], the monomer deriving the side chains (i) and the monomer deriving the side chains (ii) being present at a molar ratio ranging between 1/2 and 400/1 and the crosslinking agent being present at a ratio of 0.1–25 mol % to the total amount of the monomer (i) and monomer (ii).

8. The polymer fine particles according to claim 1, in which ultrafine particles of a free electron metal or semiconductor of a particle size ranging 1 nm–40 nm are further fixed in the core parts.

9. A crosslinked polymer which is obtained by copolymerization of (a) a poly(ethylene glycol) macromonomer represented by a formula I:

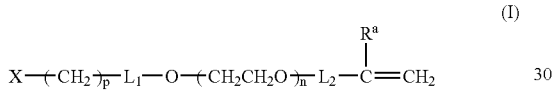

(I)

[in which X stands for hydrogen, —COOZ group (wherein Z standing for hydrogen or an organic group), —$CHR^1R^2$ (wherein $R^1$ and $R^2$ independently standing for $C_{1-6}$ alkyloxy, phenyloxy or phenyl-$C_{1-3}$ alkyloxy, or $R^1$ and $R^2$ together forming —$OCHR^1$—$CH_2O$—, R' standing for hydrogen or $C_{1-6}$ alkyl) or —CH=O, $R^a$ stands for hydrogen or $C_{1-6}$ alkyl, $L_1$ stands for methylene or carbonyl, $L_2$ stands for carbonyl, $C_{1-3}$ alkylene or $C_{1-3}$ alkylphenylene, or X—$(CH_2)_p$-$L_1$-integrally stands for hydrogen or $C_{1-6}$ alkyl, n is an integer of 2–10,000, and p is an integer of 1–5];

(b) a comonomer represented by a formula II:

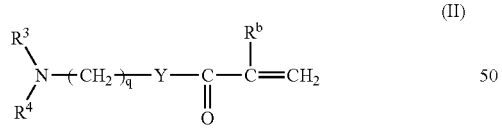

(II)

(in which $R^3$ and $R^4$ each independently stands for $C_{1-6}$ alkyl, $R^b$ stands for hydrogen or $C_{1-6}$ alkyl, Y stands for —O— or —NH—, and q is an integer of 2–6);

(c) a crosslinking agent having 2, 3, or more polymerizable unsaturated groups; and (d) optionally diluent monomer having polymerizable unsaturated group or groups, other than above (a) and (b).

10. The crosslinked polymer according to claim 9, in which no diluent monomer is present.

11. The crosslinked polymer according to claim 9, in which the poly(ethylene glycol) macromonomer (a) and the comonomer (b) are present at a molar ratio ranging from 1/400 to 2/1 and the crosslinking agent is present at a ratio of 0.1–25 mol % to the total amount of the poly(ethylene glycol) macromonomer (a) and the comonomer (b).

12. The crosslinked polymer according to claim 9, in which the crosslinking agent (c) is expressed by the formula III:

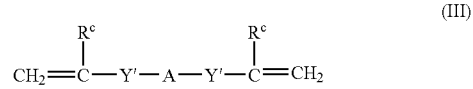

(III)

[in which $R^c$ stands for hydrogen or a $C_{1-6}$ alkyl; Y' stands for a valence bond, carbonyl or —NH—; A stands for phenylene, —$(CH_2)_\gamma$—(where $\gamma$ is an integer of 1–4), or —$(OCH_2CH_2O)_s$— (where s is an integer of 1–4].

13. A method for producing a crosslinked polymer, which comprises the steps of mixing in an inert atmosphere at room temperature (a) an aqueous solution containing a poly(ethylene glycol) macromonomer represented by the formula I:

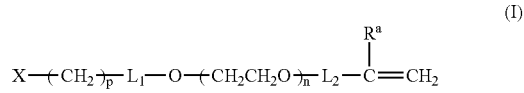

(I)

[in which X stands for hydrogen, —COOZ group (wherein Z standing for hydrogen or an organic group), —$CHR^1R^2$ (wherein $R^1$ and $R^2$ independently standing for $C_{1-6}$ alkyloxy, phenyloxy or phenyl-$C_{1-3}$ alkyloxy, or $R^1$ and $R^2$ together forming —$OCHR'$—$CH_2O$—, R' standing for hydrogen or $C_{1-6}$ alkyl) or —CH=O, $R^a$ stands for hydrogen or $C_{1-6}$ alkyl, $L_1$ stands for methylene or carbonyl, $L_2$ stands for carbonyl, $C_{1-3}$ alkylene or $C_{1-3}$ alkylphenylene, or X—$(CH_2)_p$-$L_1$-integrally stands for hydrogen or $C_{1-6}$ alkyl, n is an integer of 2–10,000, and p is an integer of 1–5] and a polymerization initiator; with (b) a comonomer represented by the formula II:

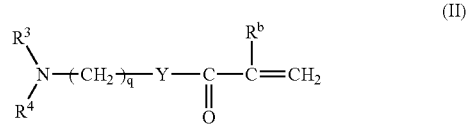

(II)

(in which $R^3$ and $R^4$ each independently stands for $C_{1-6}$ alkyl, $R^b$ stands for hydrogen or $C_{1-6}$ alkyl, Y stands for —O— or —NH—, and q is an integer of 2–6); and (c) a crosslinking agent having 2, 3, or more polymerizable unsaturated groups;

then heating the liquid mixture under stirring, to a temperature allowing initiation of the polymerization reaction; and continuing the reaction until said comonomer (b) and crosslinking agent (c) become no more detectable; using said macromonomer (a) and the comonomer (b) at a molar ratio ranging between 1/400 and 2/1, and using the crosslinking agent at a ratio of 0.1–25 mol % to the total amount of these monomers.

14. A method for producing polymer fine particles with semiconductor ultrafine particles fixed in their core parts, which comprises mixing an aqueous solution of the polymer fine particles as described in claim 1 with an aqueous solution of a chloride of Group II B or III B element of the periodic table at such a ratio that the nitrogen atoms in said polymer fine particles become 1–20 molar times that of said element and stirring the mixture; and adding thereto an aqueous solution containing at least an equivalent amount to said chloride of an alkali metal salt of a Group VI B element to further continue the reaction; using the reactants at the molar ratio between the nitrogen content of the fine particles and the Group II B or III B element ranging 1:1–1:12.

15. The production method according to claim 14, in which the chloride is cadmium chloride and the salt is sodium sulfide.

16. A method for producing polymer fine particles with gold ultrafine particles fixed in their core parts, which comprises adjusting pH of an aqueous solution of the polymer fine particles as described in claim 1 to about 6, separately preparing an aqueous solution of chloroauric acid and adjusting its pH to about 6, mixing the two aqueous solutions such that the nitrogen atoms in the polymer fine particles are 1–20 times the gold atoms in molar ratio, and stirring the mixture under the conditions sufficient to form gold fine particles and fix the same at core parts of said polymer fine particles.

* * * * *